United States Patent [19]

Dieckelmann et al.

[11] 4,115,411

[45] Sep. 19, 1978

[54] CONTINUOUS PROCESS FOR EPOXIDIZING ORGANIC COMPOUNDS CONTAINING OLEFINIC DOUBLE BONDS

[75] Inventors: Gerhard Dieckelmann, Hilden; Lutz Jeromin, Düsseldorf-Holthausen; Günther Tollkötter, Düsseldorf, all of Fed. Rep. of Germany

[73] Assignees: Henkel Kommanditgesellschaft auf Aktien, Dusseldorf-Holthausen; Deutsche Gold- und Silber-Scheideanstalt vormals Roessler, Frankfurt am Main, both of Fed. Rep. of Germany

[21] Appl. No.: 792,683

[22] Filed: May 2, 1977

[30] Foreign Application Priority Data

May 3, 1976 [DE] Fed. Rep. of Germany ....... 2619091

[51] Int. Cl.² .......................................... C07D 301/16
[52] U.S. Cl. ............................ 260/348.26; 260/348.27
[58] Field of Search ...................... 260/348.52, 348.27, 260/348.28, 348.26

[56] References Cited

U.S. PATENT DOCUMENTS 3,141,896  7/1964  Stein et al. ................. 260/348.5 L

FOREIGN PATENT DOCUMENTS 1,252,694 12/1960 France ............................ 260/348.27
1,923,392 11/1969 Fed. Rep. of Germany ...... 260/348.25
1,014,361 12/1965 United Kingdom ................ 260/502 R Primary Examiner—Norma S. Milestone
Attorney, Agent, or Firm—Hammond & Littell

[57] ABSTRACT

A continuous process for the production of epoxidized olefinic compounds comprising continuously reacting a mixture of an olefinic compound, a carboxylic acid, a strong mineral acid catalyst and a hydrogen peroxide characterized in that the reaction is conducted in the presence of an excess of water under evaporative cooling conditions whereby the desired reaction temperature is maintained, separating the epoxidized olefin from the aqueous acid solution and recycling the aqueous acid solution.

9 Claims, 1 Drawing Figure

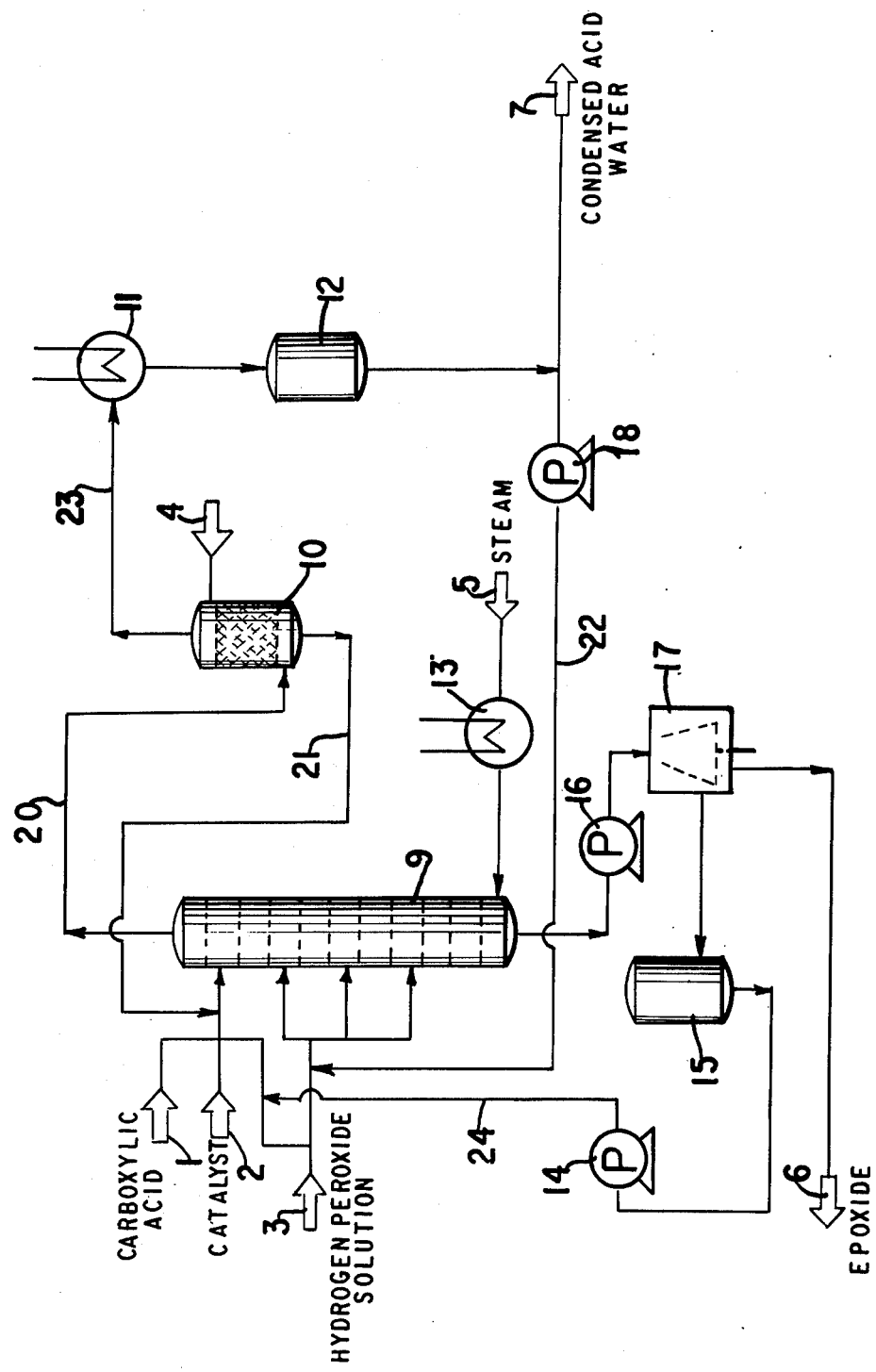

CONTINUOUS PROCESS FOR EPOXIDIZING ORGANIC COMPOUNDS CONTAINING OLEFINIC DOUBLE BONDS

RELATED ART

A batch process for epoxidizing organic compounds containing olefinic double bonds with per acids in the presence of a catalyst is described in German Pat. No. 1,152,415. Here the entrained water and the reaction water formed are distilled off during the reaction at a temperature below 100°, preferably azeotropically, with an inert organic solvent, where, if necessary, the highly acid activator dissolved in the water is neutralized at a rate depending on the amount of water removed from the reaction mixture.

In this process, which is practically only suitable for laboratory purposes, the actual purpose of removing the water from the reaction mixture and of the suggested neutralization of the highly acid activator or catalyst is to retard the undesirable epoxide ring opening reaction caused by water and highly acid catalysts. A higher consumption of starting materials must necessarily be accepted in this process because other reaction components are discharged as well with the water and the inert organic entrainer. During the epoxidization reaction a considerable amount of heat of reaction is also released, which is only partly dissipated according to German Pat. No. 1,152,145 by the azeotropic removal of the water both supplied and formed. Therefore, the remaining excess heat must be eliminated by indirect cooling, e.g. by coolers arranged outside the reaction zone, which is undesirable for the reaction. Because of above-mentioned inconveniences, a large scale application of this process is excluded.

Beyond that it is known that epoxidations with short reaction times and correspondingly higher reaction temperatures of 70° C. to 120° C. do not lead to the results obtained in the laboratory with small quantities (see FetteSeifen-Anstrichmittel, 63, 1961, p. 251–256 and ibid. 1967, p. 421–425), because it has not been possible so far to realize the exact temperature constancy of the entire reacting amount necessary for high yields of epoxides by reliable elimination of the considerable amount of heat formed during the exothermic reaction.

These known processes thus do not lead to an economical application of a large technical scale.

OBJECTS OF THE INVENTION

An object of the present invention is, therefore, to further develop the known processes for the epoxidation of organic compounds containing olefinic double bonds which contain at most 30 carbon atoms per double bond and which boil under normal pressure at least at 50° C., by treatment with percarboxylic acids, which are formed during the reaction from carboxylic acids and hydrogen peroxide in the presence of acid catalysts in such a way that the tendency to forming undesired byproducts, because of insufficient temperature control, is reduced, and high yields of epoxides are obtained, particularly with large product throughputs.

Another object of the present invention is the development of a continuous process for the production of epoxidized olefins which consists essentially of the steps of continuously reacting a mixture of an olefinic compound containing at least one olefinic double bond, said compound having at most 30 carbon atoms per double bond and a boiling point at normal pressure of at least 50° C., from 0.1 to 1 mol per double bond of said olefinic compound of a carboxylic acid having 1 to 6 carbon atoms, from 0.001 to 0.01 mol per double bond of said olefinic compound of a water-soluble strong inorganic acid, from 5 to 7 mols per double bond of said olefinic compound of water and sufficient hydrogen peroxide to give during the reaction a peracid content of from 2% to 20% by weight of the aqueous reaction phase, in a confined space at a predetermined temperature of from 50° C. to 120° C. and pressures of from 0.1 to 1.1 bar whereby the desired temperature is maintained by water evaporation, continuously withdrawing the water of evaporation, continuously withdrawing an aqueous reaction product, separating the epoxidized olefin from the aqueous acid solution, recovering said epoxidized olefin, and continuously recycling said aqueous acid solution to said reaction mixture.

These and other objects of the invention will become more apparent as the description thereof proceeds.

THE DRAWINGS

The FIGURE is a schematic flow diagram illustrating the process of the invention.

DESCRIPTION OF THE INVENTION

It was found surprisingly that the epoxidation reaction of organic compounds containing olefinic double bonds which contain at most 30 carbon atoms per double bond and which boil under normal pressure at least at 50° C. can be achieved in a continuous process, while avoiding to a great extent secondary reactions, with sufficiently short reaction times and very good constancy of the temperature, by adding to the reaction vessel 5 to 7 mols of water per mol of double bond to be epoxidized, carrying out the reaction at a predetermined temperature of from 50° C. to 120° C. and pressures of 0.1 to 1.1 bar, and eliminating the heat of reaction by evaporation of the water.

More particularly, the present invention relates to a continuous process for the production of epoxidized olefins which consists essentially of the steps of continuously reacting a mixture of an olefinic compound containing at least one olefinic double bond, said compound having at most 30 carbon atoms per double bond and a boiling point at normal pressure of at least 50° C., from 0.1 to 1 mol per double bond of said olefinic compound of a carboxylic acid having 1 to 6 carbon atoms, from 0.001 to 0.01 mol per double bond of said olefinic compound of a water-soluble strong inorganic acid, from 5 to 7 mols per double bond of said olefinic compound of water and sufficient hydrogen peroxide to give during the reaction a peracid content of from 2% to 20% by weight of the aqueous reaction phase, in a confined space at a predetermined temperature of from 50° C. to 120° C. and pressures of from 0.1 to 1.1 bar whereby the desired temperature is maintained by water evaporation,, continuously withdrawing the water of evaporation, continuously withdrawing an aqueous reaction product, separating the epoxidized olefin from the aqueous acid solution, recovering said epoxidized olefin, and continuously recycling said aqueous acid solution to said reaction mixture.

The basic idea of the process according to the invention is derived from the finding that, by evaporation of the available water, a direct evaporative cooling is effected which permits in the entire reaction mixture a uniform elimination of the heat of reaction of the epoxidation reaction so that an excellent constancy of the reaction temperature is achieved. It was found surprisingly that evaporative cooling at technically interesting throughputs permits not only a considerable reduction of undesired secondary reactions, although a considerable amount of water is present in the reaction mixture, contrary to the principle of German Pat. No. 1,152,415, but beyond that also a reduction of the reaction time is obtained, and it is possible to work at a higher reaction temperature. These advantages were not apparent to those skilled in the art.

The adjustment of the reaction temperature, which is preferably maintained below 80° C., is effected in known manner by a corresponding adjustment of the operating pressure, for example, in the head of a multitray column which is preferably used as a reaction vessel. The average reaction times range from about 1 to 2 hours in the continuous epoxidation process according to the invention.

In the multitray column the steam formed by the heat released during the reaction is conducted in counterflow to the liquid reaction partners, using the steam to mix the reaction partners on the individual trays of the column. This also results, in addition to a heat exchange, in a material exchange between the liquid and the steam, so that the reaction components, like the olefinic compounds, the epoxide formed, the hydrogen peroxide are concentrated in the liquid, as well as possibly the carboxylic acid, depending on which carboxylic acid was used for the formation of the percarboxylic acid. The relatively volatile percarboxylic acid reacts with the organic compounds containing olefinic double bonds and does not, therefore, become concentrated in the vapor phase to the extent as it could be expected in view of its vapor pressure.

The organic compound containing olefinic double bonds has at most 30 carbon atoms per double bond and a boiling point at normal pressures of at least 50° C. Olefins having 5 or less carbon atoms boil at temperatures below 50° C. Moreover, compounds with considerable branched chains likewise would boil below 50° C. under normal pressure. The organic compounds containing olefinic double bonds can be aliphatic such as alkenes, alkadienes, alkenols and alkadienols, as well as lower alkanoic acid and lower alkenoic acid esters thereof, alkenoic acids and alkadienoic acids, as well as lower alkanol and lower alkanepolyol esters thereof, and cycloaliphatic such as cycloalkene, cycloalkadiene, cycloalkenol and cycloalkadienol, as well as lower alkanoic acid and lower alkenoic acid esters thereof. Both the aliphatic and cycloaliphatic compounds can contain non-reactive hetero atoms. When alcohols are employed as starting materials, an excess of the carboxylic acid must be employed in order to replace that lost in the esterification reaction. The preferred organic compounds containing olefinic double bonds are the unsaturated fatty acid triglycerides, particularly the naturally occurring oils, such as soybean oil. These naturally occurring fatty oils are triglycerides of both saturated and unsaturated fatty acids.

The carboxylic acids which can serve as components for the formation of percarboxylic acids are those previously employed. Various monocarboxylic acids, dicarboxylic acids and polycarboxylic acids may be utilized. Preferably these carboxylic acids have from 1 to 6 carbon atoms and are free of double bonds. Alkanoic acids having from 1 to 6 carbon atoms are advantageously utilized. The preferred carboxylic acids utilized in the process according to the invention are formic acid and acetic acid, particularly formic acid. The carboxylic acids should be used in an amount of about 0.1 to 1 mol, preferably 0.2 to 0.5 mol, per mol of double bonds to be epoxidized.

The acid catalysts for accelerating the reaction between hydrogen peroxide and carboxylic acids are water-soluble strong inorganic acids, particularly mineral acids such as phosphoric acids, nitric acid or sulfuric acid. The preferred acid catalyst is sulfuric acid. The amount of water-soluble catalyst is generally between 0.001 and 0.01 mol per mol of double bonds to be epoxidized.

The dimensioning of the multitray column, particularly the determination of the number of trays to be used and of the liquid content of the individual trays, is effected according to known rules of chemical engineering and can be determined by simple tests.

In dosing the amount of water, an optimum must be found between the required evaporative cooling and the formation of per acid necessary for the reaction. The equilibrium reaction

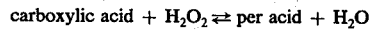

carboxylic acid + $H_2O_2$ ⇌ per acid + $H_2O$ must thus remain sufficiently displaced toward the per acid side, despite the existing large amount of water. The per acid content in the reaction mixture should preferably be in the range of 2% to 20% by weight, particularly 6% to 8% by weight related to the aqueous reaction phase. This condition has the result that a greater excess of hydrogen peroxide is required per mol of double bond to be epoxidized to obtain economically interesting reaction times than would be considered economical in the conventional batch processes. But by recirculating the unreacted hydrogen peroxide and/or the per acid, that is, recycling the aqueous phase or aqueous acid solution separated from the epoxide (the so-called acid water), and a part of the condensed vapor phase, the process can be so controlled that only the reacted hydrogen peroxide and the portions of hydrogen peroxide, carboxylic acid and catalyst removed with the spent water to sewage, have to be supplied for the reaction.

Of the entire amount of the preferably 60% to 70% hydrogen peroxide solution supplied from the outside (fresh supply), about one third together with the olefin to be epoxidized, the portions of carboxylic acid and catalyst to be replaced and the recycled acid water separated from the finished epoxide and having a residual content of hydrogen peroxide of about 20% to 25% are fed to the head of the reaction column. The remaining two thirds of the 60% to 70% hydrogen peroxide solution of the fresh supply are added to the reaction mixture in the central parts of the multitray column together with a part of the condensed acid water, obtaining from the evaporated phase by condensation, having a residual content of about 1% to 10% hydrogen peroxide, so that the content of hydrogen peroxide, related to the aqueous reaction phase, is adjusted by this measure to the range of 30% to 40% by weight.

The substantial and surprising advantage of the process according to the invention consists in that by virtue of the heat and material exchanges caused by the epoxidation reaction and the resulting steam atmosphere, which in accordance with the liquid/vapor equilibrium additionally contains some hydrogen peroxide, carboxylic acid and per acid, the epoxidation rate remains sufficiently high. Therefore, it is possible to work at higher reaction temperatures without running the risk of secondary reactions.

Another important advantage of the process according to the invention compared to the state of the art, consists in that the acid catalyst need not be neutralized. Its concentration remains constant during the reaction if care is taken that the portion of the catalyst which is removed with the epoxide from the reaction mixture and not returned is replaced when the reaction components are added. Naturally, it is not necessary in the procedure according to the invention to use the considerable amounts of solvent which are required according to process of German Pat. No. 1,152,415 for the azeotropic removal of the water, so that the process suggested here is economically more feasible for this reason alone.

The process according to the invention for the continuous epoxidation of olefin compounds is represented schematically in the attached FIGURE.

The liquid reaction partners carboxylic acid 1, catalyst 2, and concentrated hydrogen peroxide solution 3, required for the formation of per acid, are fed jointly with the substance 4 containing the olefin double bonds to the head of a multitray reaction column 9, in order that the steam formed by the evaporation of the water is conducted in counterflow to the liquid reaction components. The steam issuing from the top of column 9 is led by line 20 to wash column 10 where it is washed in counterflow to the above indicated compounds 4 to be epoxidized, thus removing mainly the per acid contained in the steam. Compound 4 is led to the head of the column 9 by line 21. Subsequently the steam issuing from the top of wash column 10 is led by line 23 to condenser 11 where it is condensed and stored temporarily in receiver 12 as condensed acid water. This condensed water contains, in addition to the water, some carboxylic acid and about 1% to 10% hydrogen peroxide. In order to recover the latter, the condensed acid water is fed partly by means of a pump 18 through line 22 to the central region of column 9. The remaining unreturned condensed acid water 7 flows to the waster water treatment plant.

The epoxide together with the aqueous phase containing unreacted hydrogen peroxide, as well as carboxylic acid with the corresponding per acid and catalyst is pumped off (16) from the sump of column 9. The aqueous phase is separated from the epoxide in a separator 17 and returned into the circuit over receiver 15, pump 14 and line 24 as acid water which still contains about 20% to 15% by weight hydrogen peroxide. The epoxide 6 is subsequently washed (not shown) and recovered.

Additional steam 5, if required, can be fed through an evaporator 13 to the sump of column 9, so that mixing of the reaction partners on the various trays in the lower part of column 9 is ensured. Lateral outlets (not shown) for the steam formed during the reaction can be provided over the height of column 9, so that the steam load does not increase excessively toward the head of column 9. Instead of the lateral outlets, condensers (not shown) can also be provided above the trays which partly condense the steam, except for the stirring steam required for the respective higher tray. However, with proper design of the column and trays, neither of these optional embodiments is required.

In order to maintain a constant reaction temperature, the head pressure in column 9 is regulated to obtain the temperatures required on the individual trays for effective evaporative cooling. To this end the liquid level on the trays is so selected, taking into account the pressure losses of the respective trays when in the dry condition, that the desired pressure profile is obtained along column 9 in dependence on the stay period of the liquid.

Due to the recirculation of the acid water and partial recirculation of the condensed acid water, only the stoichiometrically required amounts of hydrogen peroxide, that is, those amounts which are dissociated to water, are used in the process. Furthermore, only the amount of hydrogen peroxide, carboxylic acid and catalyst which are discharged either with the waste water or the epoxide must be replaced. The process is, thus, particularly economical and non-pollutant. It is thus possible to carry out the epoxidation reaction economically in the presence of large excesses of hydrogen peroxide, so that shorter reaction times and thus smaller reactors are possible.

The following examples describe the practice of the invention more fully without it being limited in any respect by the same.

EXAMPLE 1

15 kg (78 mols) of the olefin mixture (soybean oil, iodine number 132) preheated to 70° C., 215 gm of formic acid, corresponding to 0.06 mol of formic acid per mol of double bond (DB) and the portion of catalyst ($H_2SO_4$) which was subsequently discharged with the epoxide from the column were added per hour continuously over a proportioning pump unit to the upper tray of a reaction column. At the same time the acid water, which was separated from the epoxide after the reaction and which contained about 25% by weight hydrogen peroxide, and one third of the total amount of 4 kg of 70% aqueous hydrogen peroxide solution added per hour (corresponding to 1.05 mol $H_2O_2$ per mol of DB) were added on the upper tray of the column. In the central part of the column, the remaining two thirds of the hydrogen peroxide solution and a part of the condensed acid water, washed with fresh soybean oil, before condensation, with a content of about 5% by weight of hydrogen peroxide were added to the middle trays of the column in such amounts that the concentration of hydrogen peroxide in the reaction mixture during the reaction was about 30% to 40% by weight, and a per acid concentration of 8 % to 10% was maintained, with a ratio of 0.21 mol COOH and 0.005 mol $H_2SO_4$ per mol of DB. The reaction was carried out at a temperature of 70° C. and a pressure between 50 and 400 torr, depending on the tray. With a stay period in the reactor of 1.5 hours, the following results were obtained with the continuous epoxidation of the soybean oil: Epoxide value: 6.5; iodine number: 3.0. This corresponds to a yield of 87% with a recovery of 98%.

EXAMPLE 2

The continuous epoxidation corresponding to Example 1 was carried out with acetic acid as the carboxylic acid. The acetic acid was used in a molar ratio of 0.35 mol per mol of DB. 700 gm acetic acid, corresponding to 0.15 mol of acetic acid per mol of double bond, had to be replaced per hour. The reaction was carried out at a temperature of 75° C. and a pressure of 300 to 550 Torr, depending on the tray. With a stay period of 2 hours, the following results were obtained: Epoxide value: 6.2; iodine number 3.0. This corresponds to a yield of 83% with a recovery of about 98%.

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. A continuous process for the production of epoxidized olefins which consists essentially of the steps of continuously reacting a mixture consisting of:
    (a) an olefinic compound containing at least one olefinic double bond, said compound having at most 30 carbon atoms per double bond and a boiling point at normal pressure of at least 50° C.,
    (b) from 0.1 to 1 mol per mol of double bond of said olefinic compound of a carboxylic acid having 1 to 6 carbon atoms and being free of olefinic double bonds,
    (c) from 0.001 to 0.01 mol per mol of double bond of said olefinic compound of a water-soluble strong inorganic acid,
    (d) from 5 to 7 mols per mol of double bond of said olefinic compound of water, and
    (e) sufficient hydrogen peroxide to give during the reaction a peracid content of from 2% to 20% by weight of the aqueous reaction phase,
in a multitray column at a predetermined temperature of from 50° C. to 120° C. and pressures of from 0.1 to 1.1 bar whereby the desired temperature is maintained by water evaporation, wherein said aqueous reaction phase and the gaseous reaction phase are in counterflow, continuously withdrawing the steam from evaporation, continuously withdrawing an aqueous reaction product, separating the epoxidized olefin from the aqueous acid solution, recovering said epoxidized olefin, and continuously recycling said aqueous solution to said reaction, whereby said water content is maintained.

2. The continuous process of claim 1 wherein the hydrogen peroxide content in the aqueous reaction mixture is from 30% to 40% by weight.

3. The continuous process of claim 1 wherein said withdrawn steam from evaporation is contacted in counterflow with said olefinic compound and said olefinic compound is heated to said predetermined temperature.

4. The continuous process of claim 1 wherein said predetermined temperature is from 50° C. to 80° C.

5. The continuous process of claim 1 wherein said carboxylic acid is formic acid.

6. The continuous process of claim 5 wherein said formic acid is employed in an amount of from 0.2 to 0.5 mol per mol of double bond of said olefinic compound.

7. The continuous process of claim 1 wherein said water-soluble strong inorganic acid is sulfuric acid.

8. The continuous process of claim 1 wherein said olefinic compound containing at least one olefinic double bond is a naturally occurring fatty oil.

9. The continuous process of claim 8 wherein said naturally occurring fatty oil is soybean oil.

* * * * *